United States Patent
Jiang et al.

(10) Patent No.: US 10,806,566 B2
(45) Date of Patent: *Oct. 20, 2020

(54) INTRAOCULAR LENS COMPOSITIONS

(71) Applicant: NOVARTIS AG, Basel (CH)

(72) Inventors: Xuwei Jiang, Arlington, TX (US); Thomas A. Callaghan, Fort Worth, TX (US); Ahmad R. Hadba, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 210 days.

This patent is subject to a terminal disclaimer.

(21) Appl. No.: 16/005,856

(22) Filed: Jun. 12, 2018

(65) Prior Publication Data

US 2018/0353285 A1 Dec. 13, 2018

Related U.S. Application Data

(60) Provisional application No. 62/518,888, filed on Jun. 13, 2017.

(51) Int. Cl.
| | | |
|---|---|---|
| *A61F 2/16* | (2006.01) | |
| *G02B 1/04* | (2006.01) | |
| *A61L 27/16* | (2006.01) | |
| *C08F 220/28* | (2006.01) | |
| *C08L 33/08* | (2006.01) | |
| *C08L 33/24* | (2006.01) | |
| *C08L 33/12* | (2006.01) | |

(52) U.S. Cl.
CPC ............... *A61F 2/16* (2013.01); *A61L 27/16* (2013.01); *C08F 220/28* (2013.01); *G02B 1/043* (2013.01); *A61F 2240/001* (2013.01); *A61L 2430/16* (2013.01); *C08L 33/08* (2013.01); *C08L 33/12* (2013.01); *C08L 33/24* (2013.01)

(58) Field of Classification Search
CPC ........................................................ A61F 2/16
See application file for complete search history.

(56) References Cited

U.S. PATENT DOCUMENTS

| | | | | |
|---|---|---|---|---|
| 5,000,871 A | * | 3/1991 | Minayoshi | C08K 3/26 516/33 |
| 5,256,751 A | * | 10/1993 | Vanderlaan | C08F 220/26 526/304 |
| 5,470,932 A | | 11/1995 | Jinkerson | |
| 5,543,504 A | | 8/1996 | Jinkerson | |
| 7,067,602 B2 | | 6/2006 | Benz et al. | |
| 7,387,642 B2 | | 6/2008 | Benz et al. | |
| 7,947,796 B2 | | 5/2011 | Benz et al. | |
| 8,207,244 B2 | | 6/2012 | Laredo | |
| 8,262,948 B2 | | 9/2012 | Laredo et al. | |
| 8,329,775 B2 | | 12/2012 | Laredo | |
| 2004/0013704 A1 | | 1/2004 | Kabra et al. | |
| 2005/0243272 A1 | | 11/2005 | Mainster et al. | |
| 2008/0021548 A1 | | 1/2008 | Cordova et al. | |
| 2008/0029862 A1 | | 2/2008 | Filoteo, Jr. et al. | |
| 2008/0090937 A1 | | 4/2008 | Jinkerson et al. | |
| 2008/0097461 A1 | | 4/2008 | Boukhny et al. | |
| 2008/0266519 A1 | | 10/2008 | Schlueter | |
| 2009/0035225 A1 | | 2/2009 | Chatterton et al. | |
| 2009/0043105 A1 | | 2/2009 | Weinschenk, III et al. | |
| 2010/0113641 A1 | | 5/2010 | Laredo | |
| 2011/0003910 A1 | | 1/2011 | Laredo | |
| 2011/0004301 A1 | | 1/2011 | Laredo | |
| 2011/0105765 A1 | | 5/2011 | Schlueter | |
| 2011/0178202 A1 | | 7/2011 | Laredo | |
| 2011/0245442 A1 | | 10/2011 | Terrisse | |
| 2011/0257658 A1 | | 10/2011 | Chen et al. | |
| 2013/0317514 A1 | | 11/2013 | Downer | |
| 2014/0171957 A1 | | 6/2014 | McNeela et al. | |
| 2014/0257315 A1 | | 9/2014 | Wu | |
| 2018/0348404 A1 | | 12/2018 | Schlueter | |

FOREIGN PATENT DOCUMENTS

| | | |
|---|---|---|
| JP | 2000063480 A | 2/2000 |
| WO | 96/40303 A1 | 12/1996 |
| WO | 2013/040434 A1 | 3/2013 |

OTHER PUBLICATIONS

Coskun et al. J.M.S—Pure Appl. Chem., 1997, A34(1), 91-98 (Year: 1997).*

Coskun M. et al., "Synthesis and Characterization of 3-Cyclohexyloxy-2-Hydroxypropyl Acrylate and Its Homopolymer", Macromolecular Reports, A33(Suppl. 2), 117-125, (1996).

* cited by examiner

*Primary Examiner* — Michael F Pepitone

(74) *Attorney, Agent, or Firm* — Patrick M. Ryan

(57) ABSTRACT

The present invention provides novel intraocular lens compositions comprising a hydroxyl functional acrylic monomer and have a high Abbe number, minimal glistenings, and suitable mechanical properties for small incision delivery.

20 Claims, No Drawings

INTRAOCULAR LENS COMPOSITIONS

FIELD OF THE INVENTION

The field of the invention encompasses novel intraocular lens compositions.

BACKGROUND OF THE INVENTION

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The human eye functions to provide vision by transmitting and refracting light through a clear outer portion of the eye called the cornea, and further focusing the image by way of a lens onto the retina at the back of the eye. The quality of the focused image depends on many factors including the size, shape and length of the eye, and the shape and transparency of the cornea and lens. When trauma, age, disease and/or another malady cause an individual's natural crystalline lens to become less transparent, vision deteriorates because of the diminished light that is transmitted to the retina. This deficiency in the lens of the eye is often referred to as a cataract. The treatment for this condition is surgical removal of the natural crystalline lens and implantation of an intraocular lens (IOL). Alternatively, IOLs can be used to work in conjunction with the existing lens in the eye to change the eye's optical power as a treatment for, e.g., myopia or nearsightedness.

While early IOLs were made from hard plastic such as polymethylmethacrylate (PMMA), soft, foldable IOLs made from silicone, soft acrylics and hydrogels have become increasingly popular. However, any compositions from which IOLs are made must provide the IOL with certain important properties including acceptable mechanical properties that allow delivery of the lens into the eye, minimized glistening (inclusions in the composition of the IOL), a relatively high refractive index value, and a high Abbe number. There is a need in the art for IOL compositions that convey these properties. The present invention provides such IOL material compositions.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects defined in the appended claims.

One embodiment of the present invention encompasses a copolymeric material for use in an intraocular lens, wherein the copolymeric material is formed by polymerizing a composition comprising 80-99 weight % of one or more monomers of Formula I:

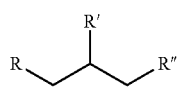

Formula I

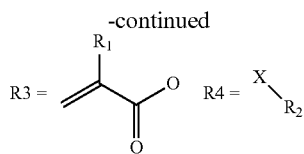

wherein R, R', and R" are selected from the group consisting of hydroxyl, $R_3$, and $R_4$, and provided that R, R', and R" are all different; X is selected from the group consisting of O, C and S; $R_1$ is selected from the group consisting of H and $C_1$-$C_3$ alkyl; and $R_2$ is a saturated $C_5$-$C_{12}$ alkyl (which may be linear, branched, cyclic or a combination thereof). In preferred embodiments, R is $R_3$; $R_1$ is hydrogen or methyl; R" is $R_4$; X is O; and $R_2$ is a saturated $C_6$-$C_8$ alkyl. In exemplary embodiments, $R_2$ is selected from the group consisting of norbonanemethyl (NHPA) (Formula 1a), cyclohexylmethyl (CMHPA) (Formula 1b), cyclohexyl (CHHPA) (Formula 1c), and cyclohexylethyl (CEHPA) (Formula 1d), as shown below:

Formula Ia

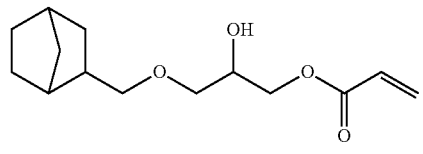

(NHPA)

Formula 1b

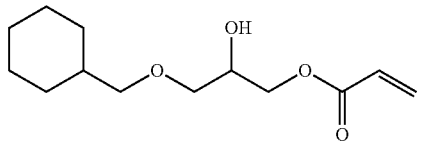

(CMHPA)

Formula 1c

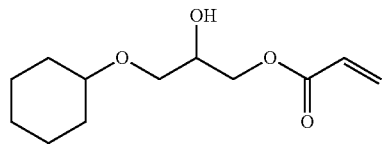

(CHHPA)

Formula 1d

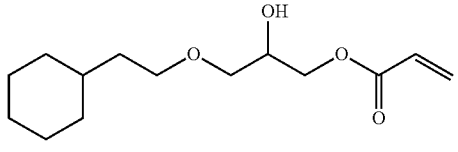

(CEHPA)

Another embodiment of the invention provides a copolymer composition for use in an intraocular lens, wherein the copolymer composition is formed by polymerizing a composition comprising 50-95 weight % of one or more monomers of Formula I and a hydrophilic acrylic monomer. In this embodiment, the hydrophilic acrylic monomer helps to minimize or eliminate the presence of glistenings in the resulting copolymer. The hydrophilic acrylic monomers suitable for use in the present invention contain at least one reactive, unsaturated functional group. Preferably, the reactive unsaturated functional group is a vinyl, acrylate or methacrylate group. The homopolymers of the hydrophilic monomers suitable for use in the materials of the present invention have an equilibrium water content of at least 10%, and preferably at least 25%, by weight as determined gravimetrically in deionized water at ambient conditions. Suitable hydrophilic acrylic monomers for use in the present invention include: 2-hydroxyethyl acrylate; 2-hydroxyethyl methacrylate; 2-N-ethylacrylate pyrrolidone; 2,3-dihydroxypropyl acrylate; 2,3-dihydroxypropyl methacrylate; 2-N-vinyl pyrrolidone; N-hydroxyethylacrylamide; N,N-dimethylacrylamide; and N,N-bis(2-hydroxyethyl) acrylamide.

In preferred embodiments, the hydrophilic acrylic monomer is selected from the group consisting of: 2-hydroxyethyl methacrylate: 2-hydroxyethyl acrylate; and N,N-dimethylacrylamide.

The copolymer compositions of the invention further comprise a cross-linking agent and a UV-absorber. Optionally, the copolymer compositions comprise a visible-light absorber such as a blue-light blocking chromophore.

The copolymer materials of the present invention are characterized by a relatively high refractive index (measured when hydrated at 35° C.) and a high Abbe number. The copolymer materials of the invention generally have a refractive index of 1.45-1.52, and preferably 1.47-1.52. The copolymer materials of the invention generally have an Abbe number ≥45, and preferably ≥50. These and other aspects and uses of the invention will be described in the detailed description.

DETAILED DESCRIPTION OF THE INVENTION

The methods described herein may employ, unless otherwise indicated, descriptions and synthesis of organic acrylic materials containing hydroxyl and saturated aliphatic groups, as well as the manufacture and delivery of intraocular lenses, all of which are within the skill of those who practice in the art. Specific illustrations of suitable techniques can be had by reference to the examples herein. However, equivalent conventional procedures can, of course, also be used. Such conventional techniques and descriptions can be found in standard laboratory manuals, and patents and published applications such for as organic synthesis: *Advanced Organic Chemistry*, Carey and Sundberg, Springer (2005); *Classics in Total Synthesis*, Nicolaou and Sorenson, Wiley-VCH (1998); *Elements of Synthesis Planning*, Hoffman, Springer (2009); *Modern Organic Synthesis—An Introduction*, Zweifel and Nantz, W. H. Freeman (2007), and *Organic Synthesis—State of the Art 2003-2005*, Taber, Wiley-Interscience (2006); for hydrophobic and hydrophilic foldable lenses: U.S. Pat. Nos. 7,947,796, 7,387, 642, 7,067,602, US Pub Nos. 2008/0021548, 2007/01840089, and 2004/0013704; and for delivery of IOLs: US Pub Nos. 2014/0257315, 2014/0171957, 2013/0317514, 2011/0257658, 2008/0029862, and 2008/0097461, all of which are incorporated herein by reference in their entirety for all purposes. Before the present IOL compositions are described, it is to be understood that this invention is not limited to the specific synthesis regimes described, as such may, of course, vary. It is also to be understood that the terminology used herein is for the purpose of describing particular aspects only and is not intended to limit the scope of the present invention, which will be limited only by the appended claims.

Note that as used in the present specification and in the appended claims, the singular forms "a," "an," and "the" include plural referents unless the context clearly dictates otherwise. Thus, for example, reference to "a composition" refers to one or mixtures of compositions, and reference to "an assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the reference and which might be used in connection with the presently described invention.

Where a range of values is provided, it is understood that each intervening value between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes both of the limits, ranges excluding either of those included limits are also included in the invention.

In the following description, numerous specific details are set forth to provide a more thorough understanding of the present invention. However, it will be apparent to one of skill in the art upon reading the specification that the present invention may be practiced without one or more of these specific details. In other instances, well-known features and procedures well known to those skilled in the art have not been described in order to avoid obscuring the invention.

The Invention

The present invention provides in one embodiment novel intraocular lens (IOL) materials comprising a hydroxyl functional acrylic monomer at a weight % of 80-99%, possessing a high Abbe number, minimal glistenings, and suitable mechanical properties for use in small incision delivery. In another embodiment, the present invention provides novel intraocular lens compositions comprising a hydroxyl functional acrylic monomer at a weight % of 50-95% and a hydrophilic acrylic monomer. The IOLs of this alternative embodiment also possesses a high Abbe number, minimal glistenings, and suitable mechanical properties for use in small incision delivery.

The IOL materials of the present invention provide a number of benefits over current IOL compositions, including but not limited to: a relatively high refractive index value after hydration; being substantially free of glistenings when equilibrated in water at 45° C. followed by cooling to eye temperature (35° C.); and possessing suitable mechanical properties for delivery through small (≤2.2 mm) incisions.

The IOL materials of the present invention are copolymers formed from compositions comprising a hydroxyl functional acrylic monomer of Formula I:

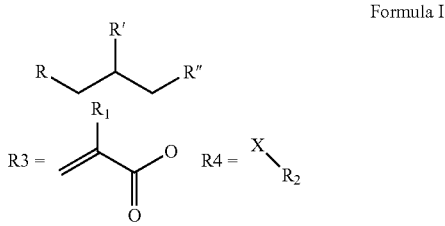

Formula I wherein R, R', and R" are selected from the group consisting of hydroxyl, $R_3$, and $R_4$, and provided that R, R', and R" are all different; X is selected from the group consisting of O, C and S; $R_1$ is selected from the group consisting of H and $C_1$-$C_3$ alkyl; and $R_2$ is a saturated $C_5$-$C_{12}$ alkyl (which may be linear, branched, cyclic or a combination thereof). In preferred embodiments, R is $R_3$; R' is hydroxyl or methyl; R" is $R_4$; X is O; $R_1$ is H or $CH_3$; and $R_2$ is a saturated $C_6$-$C_8$ alkyl. In exemplary embodiments, $R_2$ is selected from the group consisting of norbonanemethyl (NHPA) (Formula 1a) [for Formula 1a: R=—X—$R_2$; X=O; $R_2$=

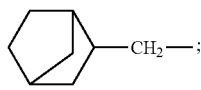

R'=OH; R"=$R_3$; and $R_1$=H], cyclohexylmethyl (CM-HPA) (Formula 1b), cyclohexyl (CHHPA) (Formula 1c), and cyclohexylethyl (CEHPA) (Formula 1d). In one embodiment, the copolymer composition is prepared by polymerizing a composition comprising 80-99 weight % of one or more monomers of Formula I. In another embodiment, the copolymer composition comprises a mixture of monomers of Formula I having $R_1$=H and $R_1$=$CH_3$.

In another embodiment, the copolymer composition of the present invention is prepared by polymerizing a composition comprising 50-95 weight % of a monomer of Formula I and a hydrophilic acrylic monomer. In this embodiment, the hydrophilic acrylic monomer helps to minimize or eliminate the presence of glistenings in the resulting copolymer. The hydrophilic acrylic monomers suitable for use in the present invention contain at least one reactive, unsaturated functional group. Preferably, the reactive unsaturated functional group is a vinyl, acrylate or methacrylate group. The homopolymers of the hydrophilic monomers suitable for use in the materials of the present invention have an equilibrium water content of at least 10%, and preferably at least 25%, by weight as determined gravimetrically in deionized water at ambient conditions. Suitable hydrophilic acrylic monomers for use in the present invention include: 2-hydroxyethyl acrylate; 2-hydroxyethyl methacrylate; 2-N-ethylacrylate pyrrolidone; 2,3-dihydroxypropyl acrylate; 2,3-dihydroxypropyl methacrylate; 2-N-vinyl pyrrolidone; N-hydroxyethylacrylamide; N,N-dimethylacrylamide; and N,N-bis(2-hydroxyethyl) acrylamide. The amount of hydrophilic acrylic monomer is generally 0.5-45 wt. %, and preferably 5-20 wt. %.

In preferred embodiments, the hydrophilic acrylic monomer is selected from the group consisting of 2-hydroxyethyl methacrylate; 2-hydroxyethyl acrylate; and N,N-dimethylacrylamide.

In addition to the monomer of Formula I and any hydrophilic monomer, the copolymer compositions of the present invention contain a cross-linking agent. The cross-linking agent used in the copolymers of this invention may be any terminally ethylenically unsaturated compound having more than one unsaturated group. Combinations of cross-linking monomers are also suitable. Suitable cross-linking agents include, for example: ethylene glycol diacrylate; ethylene glycol dimethacrylate; diethylene glycol diacrylate; diethylene glycol dimethacrylate; triethylene glycol diacrylate; triethylene glycol dimethacrylate; allyl acrylate; allyl methacrylate; 1,3-propanediol diacrylate; 1,3-propanediol dimethacrylate; 1,6-hexanediol diacrylate; 1,6-hexanediol dimethacrylate; 1,4-butanediol diacrylate; 1,4-butanediol dimethacrylate; poly(ethylene oxide)diacrylate (number average molecular weight 600-1000); poly(ethylene oxide) dimethacrylate (number average molecular weight 600-1000); and the like. Generally, the amount of the cross-linking component is at least 0.1% (weight). Preferably the concentration of the cross-linking agent is 0.2-20 wt. % and more preferably 1.0-10 wt. %.

The IOL materials of the present invention also comprise a UV absorber and optionally comprise a visible light absorber. In preferred embodiments, the UV and visible light absorbers are covalently bound to the polymer network. Many UV light absorbers are known and include benzotriazoles, triazines, and benzophenones. For example, the benzotriazole 2-(2H-benzo[d][1,2,3]triazol-2-yl)-4-methyl-6-(2-methylallyl) phenol (oMTP) is a UV absorber known to be useful in IOL materials, as are compounds such as those disclosed in U.S. Pat. No. 8,262,948 and US Pub. Nos. 2011/0105765; 2011/0004301; 2010/0113641; 2009/0035225; and 2008/0266519. Visible light absorbers typically contain olefinic polymerizable groups and include (E)-4-((2-hydroxy-5-methylphenyl)diazenyl)phenyethyl methacrylate and (E)-4-hydroxy-3-((4-(2-(methacryloyloxy)ethyl)phenyl)diazenyl)phenethyl methacrylate, and compounds such as those disclosed in U.S. Pat. Nos. 8,207,244 and 8,329,775; and US Pub. Nos. 2011/0003910; 2009/0043105; and 2011/0178202. Alternatively, a combination UV/visible light absorber may be employed such as 3-(5-fluoro-2H-benzo[d][1,2,3]triazol-2-yl)-2-hydroxy-5-methoxybenzyl methacrylate; 3-(2H-benzo[d][1,2,3]triazol-2-yl)-2-hydroxy-5-methoxybenzyl methacrylate; 3-(5-chloro-2H-benzo[d][1,2,3]triazol-2-yl)-2-hydroxy-5-methoxybenzyl methacrylate; 2-hydroxy-5-methoxy-3-(5-methoxy-2H-benzo[d][1,2,3]triazol-2-yl)benzyl methacrylate; 2-hydroxy-5-methoxy-3-(5-methyl-2H-benzo[d][1,2,3]triazol-2-yl)benzyl methacrylate; and 2-hydroxy-5-methyl-3-(5-(trifluoromethyl)-2H-benzo[d][1,2,3]triazol-2-yl)benzyl methacrylate. Also, the IOLs of the present invention in addition to UV light absorbers may comprise blue light chromophores as disclosed in U.S. Pat. Nos. 5,470,932 and 5,543,504; and US Pub. Nos. 2005/0243272 and 2008/0090937. The concentration of UV and/or visible light absorbers will depend on the compound used; however, each of these components of the IOL material typically is in the range of e.g., 0.01-3.0 wt %, or more preferably 0.04-2.0 wt %.

The copolymer materials of the present invention are prepared by polymerizing the monomeric components described above using conventional polymerization initiators such as thermal initiators and photoinitiators. For example, thermal initiators include peroxy free-radical initiators, such as t-butyl (peroxy-2-ethyl)hexanoate and di-(tert-butylcyclohexyl) peroxydicarbonate (commercially available as Perkadox® 16 from Akzo Chemicals Inc., Chicago, Ill.). photoinitiators such as phenylbis (2,4,6-trimethylbenzoyl)phosphine oxide (IRGACURE® 819), 1-hydroxy-cyclohexyl-phenyl-ketone, 2-hydroxy-2-methyl-1-phenyl-propanone, methylbenzoylformate, α,α-diemthoxy-α-phenylacetophenone and others may be used. Alternatively, radical initiators such as organic peroxide compounds, azo compounds may be used. The concentration of the curing agent will depend upon the agent used, but typically is in the range of e.g., 0.05-5.0 wt %, or more preferably 0.1-2.0 wt %. As is customary for purposes of calculating component amounts, the initiator weight is not included in the formulation weight % calculation.

The IOL compositions of the present invention can be used in all types of IOLs, including single-piece and multipiece IOLs, pseudophakic and phakic IOLs, as well as monofocal and diffractive and refractive multifocal IOLs. Further, the IOLs of the present invention can be delivered using methods and systems known in the art, including the INTREPID® AUTOSERT® IOL injector (Alcon, Fort Worth, Tex.) and the ULTRASERT® Pre-loaded Delivery System (Alcon, Fort Worth, Tex.), as well as the delivery methods and systems disclosed in, e.g., US Pub Nos. 2014/0257315, 2014/0171957, 2013/0317514, 2011/0257658, 2008/0029862, and 2008/0097461.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Synthesis of cyclohexyl glycidyl ether: To a 3 L jacketed reactor equipped with a mechanical stirrer and thermal couple were charged 1 kg of sodium hydroxide and 1 L distilled water. The mixture was stirred and cooled to room temperature, followed by the addition of 20 g tetrabutylammonium hydrogensulfate (TBAS). The mixture was then cooled to <10° C. and 1127 g epichlorohydrin (12.25 mol) was added slowly over one hour. After the addition, 520 g cyclohexanol (5.20 mol) was added dropwise with temperature of the reaction mixture being kept below 15° C. during addition. After the addition, the reaction mixture was stirred at 15° C. overnight and then at room temperature for two days. The reaction mixture was then diluted by the addition of 2 L DI water and extracted with hexanes (1 L×5). Dichloromethane was then used to extract the aqueous layer (500 ml×4). The combined organic layer was dried over $MgSO_4$ and concentrated. The crude product was then vacuum distilled using a falling film evaporator with ethyl acetate as refluxing solvent. The clear colorless distillate was then fractionally distilled under vacuum and the fraction at 30° C./60 mTorr was collected as clear liquid (495 g, yield: 61%).

Synthesis of cyclohexyloxy-hydroxypropyl acrylate (CHHPA): To a 1 L three-neck RBF equipped with an oxygen inlet and thermometer was charged 306 g of acrylic acid (4.25 mol) and anhydrous pyridine (25 mL). The mixture was stirred under an oxygen blanket and heated to 50° C. To the stirred solution was then added cyclohexyl glycidyl ether (172 g, 1.1 mol) over one hour. After the addition, the mixture was stirred at 60° C. until cyclohexyl glycidyl ether was no longer detectable by GC-FID. After cooling to room temperature, the reaction mixture was diluted in hexanes/ethyl acetate (1/1:v/v, 1 L) and extracted with 3N NaOH in 15 wt % NaCl until the aqueous layer was basic, followed by extraction with 15% NaCl solution until the aqueous layer was neutral. The organic layer was then dried over sodium sulfate and concentrated to give the crude product as a colorless oil which was then purified on silica gel using hexanes/ethyl acetate as eluent.

Example 2

Synthesis of cyclohexylmethyl glycidyl ether: To a 3 L jacketed reactor equipped with mechanical stirrer and thermal couple were charged 1 kg of sodium hydroxide and 1 L distilled water. The mixture was stirred and cooled to room temperature, followed by the addition of 20 g tetrabutylammonium hydrogensulfate (TBAS). The mixture was then cooled to <10° C., and 1 kg epichlorohydrin was added slowly over one hour. After the addition, 505 g cyclohexymethanol (4.43 mol) was added in slowly with the temperature of the reaction mixture being kept below 15° C. during addition. After the addition, the reaction mixture was stirred at 15° C. overnight and then at room temperature for two days. The reaction mixture was then diluted by the addition of 2 L DI water and extracted with hexanes (1 L×5). The combined organic layer was dried over sodium sulfate and concentrated. The crude product was then vacuum distilled using a falling film evaporator with ethyl acetate as refluxing solvent. The clear colorless distillate was fractionally distilled under vacuum and the fraction at 30° C./50 mTorr was collected as clear liquid (557 g, yield: 74%).

Synthesis of cyclohexylmethoxy-hydroxypropyl acrylate (CMHPA): To a 1 L three-neck RBF equipped with an oxygen inlet and thermometer was charged 584 g of acrylic acid (8.1 mol) and anhydrous pyridine (30 mL). The mixture was stirred under an oxygen blanket and heated to 50° C. To the stirred solution was added cyclohexylmethyl glycidyl ether (255 g, 1.5 mol) over one hour. After the addition, the mixture was stirred at 60° C. until cyclohexylmethyl glycidyl ether was no longer detectable by GC-FID. After cooling to room temperature, the reaction mixture was diluted in hexanes/ethyl acetate (1/1:v/v, 1.5 L) and extracted with 3N NaOH in 15 wt % NaCl until the aqueous layer was basic, followed by extraction with 15% NaCl solution until the aqueous layer was neutral. The organic layer was then dried over sodium sulfate and concentrated to give the crude product as a colorless oil which was then purified on silica gel using hexanes/ethyl acetate as eluent.

Example 3

Synthesis of 2-cyclohexylethyl glycidyl ether: To a 3 L jacketed reactor equipped with mechanical stirrer and thermal couple were charged 1 kg of sodium hydroxide and 1 L distilled water. The mixture was stirred and cooled to room temperature, followed by the addition of 20 g tetrabutylammonium hydrogensulfate (TBAS). The mixture was then cooled to <10° C. and 910 epichlorohydrin was added slowly over an hour. After the addition, 504 g cyclohexyethanol (3.95 mol) was added in 50 ml portions with the temperature of the reaction mixture being kept below 15° C. during addition. The reaction mixture was then stirred at 15° C. over the weekend. The reaction mixture was diluted by the addition of 2 L DI water and extracted with hexanes (1 L×5). The combined organic layer was dried over sodium sulfate and concentrated. The crude product was then vacuum distilled using a falling film evaporator with ethyl acetate as refluxing solvent. The clear colorless distillate was then fractionally distilled under vacuum and the fraction at 40° C./70 mTorr was collected (655 g, yield: 91%).

Synthesis of cyclohexylethoxy-hydroxypropyl acrylate (CEHPA): To a 1 L three-neck RBF equipped with an oxygen inlet and thermometer was charged 674 g of acrylic acid (9.4 mol) and anhydrous pyridine (30 mL). The mixture was stirred an under oxygen blanket and heated to 50° C. To the stirred solution was then added 2-cyclohexylethyl glycidyl ether (370 g, 2.0 mol) over one hour. After the addition, the mixture was stirred at 60° C. until 2-cyclohexylethyl glycidyl ether was no longer detectable by GC-FID. After cooling to room temperature, the reaction mixture was diluted in hexanes/ethyl acetate (1/1:v/v, 2 L) and extracted with 3N NaOH in 15 wt % NaCl until the aqueous layer was basic, followed by extraction with 15% NaCl solution until the aqueous layer was neutral. The organic layer was then dried over sodium sulfate and concentrated to give the crude product as colorless oil which was then purified on silica gel using hexanes/ethyl acetate as eluent.

Example 4

Synthesis of 2-norbornanemethyl glycidyl ether: To a 3 L jacketed reactor equipped with a mechanical stirrer and thermal couple were charged 1 kg of sodium hydroxide and 1 L distilled water. The mixture was stirred and cooled to room temperature, followed by the addition of 20 g tetrabutylammonium hydrogensulfate (TBAS). The mixture was then cooled to <10° C. and 1090 g epichlorohydrin was added slowly over one hour. After the addition, 700 mL of 2-Norbornanemethanol was added in 50 ml portions with the temperature of the reaction mixture being kept below 15° C. during addition. After the addition, the reaction mixture was stirred at 15° C. over the weekend. The reaction mixture was diluted by the addition of 2 L DI water and extracted with hexanes (1 L×5). The combined organic layer was dried over sodium sulfate and concentrated. The crude product was then vacuum distilled using a falling film evaporator with water as refluxing solvent. The clear colorless distillate was fractionally distilled under vacuum and the fraction at 70° C. 180 mTorr was collected (788 g, yield: 78%).

Synthesis of norbornanemethoxy-hydroxypropyl acrylate (NHPA): To a 1 L three-neck RBF equipped with oxygen inlet and thermometer was charged 302 g of acrylic acid (4.2 mol) and anhydrous pyridine (15 mL). The mixture was stirred under an oxygen blanket and heated to 50° C. To the stirred solution was then added 2-norbornanemethyl glycidyl ether (165 g, 0.9 mol) over one hour. After the addition, the mixture was stirred at 60° C. until 2-norbornanemethyl glycidyl ether was no longer detectable by GC-FID. After cooling to room temperature, the reaction mixture was diluted in hexanes/ethyl acetate (1/1:v/v, 2 L) and extracted with 3N NaOH in 15 wt % NaCl until the aqueous layer was basic, followed by extraction with 15% NaCl solution until the aqueous layer was neutral. The organic layer was dried over sodium sulfate and concentrated to give the crude product as colorless oil which was then purified on silica gel using hexanes/ethyl acetate as eluent.

Example 5

Crosslinked Polymers. The monomers cyclohexyloxy-hydroxypropyl acrylate (CHHPA), cyclohexylmethoxy-hydroxypropyl acrylate (CMHPA), cyclohexylethoxy-hydroxypropyl acrylate (CEHPA), and norbonanemethoxy-hydroxypropyl acrylate (NHPA) were synthesized as detailed in Examples 1-4 and then formulated as shown in Table 1. Test samples measuring 1.0 mm in thickness were blue-light cured (using 1% benzoyl peroxide for Formulation 5 and 0.3% IRGACURE® 819 [phenylbis (2,4,6-trimethylbenzoyl)phosphine oxide] for all others) at 55° C. for 1 hour. Samples were extracted in acetone for 6 hours at room temperature and then dried slowly at ambient temperature for 20 hours, followed by vacuum (0.1 mm Hg) for a minimum of 20 hours at 70° C. Weight percent extractables, refractive index values, and tensile properties are shown in Table 2 (FIG. 3). In Table 2, pre-hydrated samples from Formulation 1 and dry samples from all other Formulations were used in tensile tests. Tensile tests were carried out in a 18° C. water bath with a 3-minute soak prior to testing. Refractive index (RI) measurements were carried out at 35° C. using hydrated test samples.

TABLE 1

| Component | Formulation | | | | | | |
|---|---|---|---|---|---|---|---|
| | 1 | 2 | 3 | 4 | 5 | 6 | 7 |
| CHHPA | | 95.7 | | | | | |
| CMHPA | | | | 95.7 | 94.0 | 55.7 | |
| CEHPA | | | 95.7 | | | 40.0 | 80.7 |
| NHPA | 95.7 | | | | | | |
| HEMA | | | | | | | 15.0 |
| TEGDA | 2.5 | 2.5 | 2.5 | 2.5 | 4.2 | 2.5 | 2.5 |
| oMTP | 1.8 | 1.8 | 1.8 | 1.8 | 1.8 | 1.8 | 1.8 |

CHHPA = cyclohexyloxy-hydroxypropyl acrylate
CMHPA = cyclohexylmethoxy-hyroxypropyl acrylate
CEHPA = cyclohexylethoxy-hyroxypropyl acrylate
NHPA = norbonanemethoxy-hyroxypropyl acrylate
HEMA = 2-hydroxyethyl methacrylate
TEGDA = triethylene glycol methacrylate
oMTP = 2-(2H-benzo[d][1,2,3]triazol-2-yl)-4-methyl-6-(2-methylallyl)phenol

TABLE 2

| Formulation No. | % Extractables (N ≥12) | EWC (%) (N ≥6) | R.I at 589 nm (hydrated) | Young's Modulus (MPA) | Strain at Break (%) | 25% Secant Modulus (MPa) | 100% Secant Modulus (MPa) | Stress at Break (MPa) | ABBE | MV density (vac/mm²) |
|---|---|---|---|---|---|---|---|---|---|---|
| 1 | 2.7 ± 0.1 | 2.8 ± 0.1 | 1.505 | 33.7 ± 7.7 | 184 ± 7 | 2.3 ± 0.1 | 1.2 ± 0.0 | 4.1 ± 0.3 | 56 | 15.8 ± 10.2 |
| 2 | 2.9 ± 0.1 | 4.2 ± 0.1 | 1.496 | 134 ± 28 | 174 ± 5 | 9.3 ± 0.3 | 4.1 ± 0.1 | 8.4 ± 0.4 | 55 | 0 ± 0 |
| 3 | 2.2 ± 0.2 | 3.1 ± 0.1 | 1.496 | 13.4 ± 3.8 | 121 ± 16 | 1.1 ± 0.1 | 0.9 ± 0.0 | 1.3 ± 0.3 | 55 | N/A |
| 4 | 1.9 ± 0.1 | 3.1 ± 0.1 | 1.496 | 42.3 ± 6.0 | 177 ± 8 | 3.2 ± 0.1 | 1.7 ± 0.1 | 4.8 ± 0.4 | 56 | 4.7 ± 13.3 |
| 5 | 2.1 ± 0.1 | 3.0 ± 0.1 | 1.496 | | | | | | 55 | 0.3 ± 1.0 |
| 6 | 1.9 ± 0.1 | 3.1 ± 0.1 | 1.496 | 20.1 ± 1.0 | 146 ± 4 | 1.6 ± 0.0 | 1.2 ± 0.0 | 2.5 ± 0.2 | 55 | 3.1 ± 3.2 |
| 7 | 1.8 ± 0.1 | 4.0 ± 0.1 | 1.496 | 31.2 ± 4.7 | 169 ± 5 | 3.3 ± 0.1 | 1.9 ± 0.1 | 4.6 ± 0.2 | 56 | 0.5 ± 1.3 |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A copolymeric material for use in an intraocular lens, wherein the copolymeric material is formed by polymerizing a composition comprising 80-99 weight % of one or more monomers of Formula I:

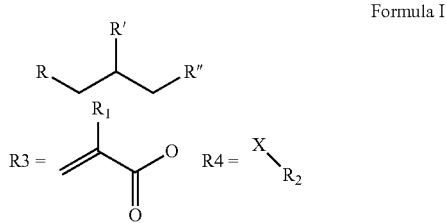

Formula I wherein R, R', and R" are selected from the group consisting of hydroxyl, $R_3$, and $R_4$, and provided that R, R', and R" are all different; R is $R_3$, R' is hydroxyl, R" is $R_4$, X is O, $R_1$ is H, and $R_2$ is selected from the group consisting of norbonanemethyl, cyclohexylmethyl, and cyclohexylethyl.

2. The copolymeric material of claim 1, wherein $R_2$ is norbonanemethyl.

3. The copolymeric material of claim 1, wherein $R_2$ is cyclohexylmethyl.

4. The copolymeric material of claim 1, wherein $R_1$ is H and $R_2$ is cyclohexylethyl.

5. The copolymeric material of claim 1, further comprising a cross-linking agent.

6. The copolymeric material of claim 1 wherein the copolymeric material has a refractive index when measured hydrated at 35° C. of 1.45-1.52.

7. The copolymeric material of claim 6, wherein the copolymeric material has a refractive index when measured hydrated at 35° C. of 1.47-1.52.

8. The copolymeric material of claim 1, wherein the copolymeric material has an Abbe number ≥45.

9. The copolymeric material of claim 8, wherein the copolymeric material has an Abbe number ≥50.

10. A copolymeric material for use in an intraocular lens, wherein the copolymeric material is formed by polymerizing a composition comprising 50-95 weight % of one or more monomers of Formula I and a hydrophilic acrylic monomer:

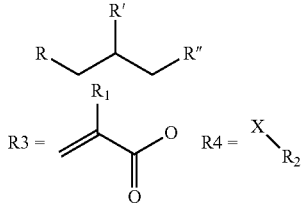

Formula I wherein R, R', and R" are selected from the group consisting of hydroxyl, $R_3$, and $R_4$, and provided that R, R', and R" are all different; X is selected from the group consisting of 0, C and S; $R_1$ is selected from the group consisting of H and $C_1$-$C_3$ alkyl; and $R_2$ is a saturated $C_5$-$C_{12}$ alkyl.

11. The copolymeric material of claim 10, wherein R is $R_3$; R' is hydroxyl; R" is $R_4$; X is O; $R_1$ is H or $CH_3$; and $R_2$ is a saturated $C_6$-$C_8$ alkyl.

12. The copolymeric material of claim 11, wherein $R_1$ is H and $R_2$ is norbonanemethyl.

13. The copolymeric material of claim 11, wherein $R_1$ is H and $R_2$ is cyclohexylmethyl.

14. The copolymeric material of claim 11, wherein $R_1$ is H and $R_2$ is cyclohexyl.

15. The copolymeric material of claim 11, wherein $R_1$ is H and $R_2$ is cyclohexylethyl.

16. The copolymeric material of claim 10, wherein the hydrophilic acrylic monomer is selected from the group consisting of: 2-hydroxyethyl methacrylate; 2-hydroxyethyl acrylate; and N,N-dimethylacrylamide.

17. The copolymeric material of claim 10 wherein the copolymeric material has a refractive index when measured hydrated at 35° C. of 1.45-1.52.

18. The copolymeric material of claim 17, wherein the copolymeric material has a refractive index when measured hydrated at 35° C. of 1.47-1.52.

19. The copolymeric material of claim 10, wherein the copolymeric material has an Abbe number ≥45.

20. The copolymeric material of claim 19, wherein the copolymeric material has an Abbe number ≥50.

* * * * *